(12) United States Patent
Hong et al.

(10) Patent No.: US 10,688,482 B2
(45) Date of Patent: Jun. 23, 2020

(54) METHOD FOR OLEFIN OLIGOMERIZATION

(71) Applicant: LG CHEM, LTD., Seoul (KR)

(72) Inventors: Yoon Ki Hong, Daejeon (KR); Yong Ho Lee, Daejeon (KR); Eun Ji Shin, Daejeon (KR); Ki Soo Lee, Daejeon (KR); Jin Young Park, Daejeon (KR); Seok Pil Sa, Daejeon (KR); Seul Ki Im, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/544,236

(22) PCT Filed: Feb. 5, 2016

(86) PCT No.: PCT/KR2016/001325
§ 371 (c)(1),
(2) Date: Jul. 17, 2017

(87) PCT Pub. No.: WO2016/129901
PCT Pub. Date: Aug. 18, 2016

(65) Prior Publication Data
US 2018/0009727 A1    Jan. 11, 2018

(30) Foreign Application Priority Data

Feb. 12, 2015  (KR) .................. 10-2015-0021784
Dec. 10, 2015  (KR) .................. 10-2015-0176277

(51) Int. Cl.
| | | |
|---|---|---|
| *C07C 2/24* | (2006.01) |
| *B01J 31/24* | (2006.01) |
| *C08K 5/00* | (2006.01) |
| *C08K 5/17* | (2006.01) |
| *B01J 31/18* | (2006.01) |
| *B01J 31/02* | (2006.01) |
| *B01J 31/04* | (2006.01) |
| *B01J 31/14* | (2006.01) |
| *C07C 2/32* | (2006.01) |
| *C08F 210/16* | (2006.01) |
| *C08F 2/40* | (2006.01) |
| *C08F 4/69* | (2006.01) |
| *C08F 10/00* | (2006.01) |
| *C08K 5/05* | (2006.01) |
| *C07F 9/50* | (2006.01) |
| *B01J 35/00* | (2006.01) |
| *B01J 37/04* | (2006.01) |
| *C08F 10/02* | (2006.01) |

(52) U.S. Cl.
CPC ....... *B01J 31/2409* (2013.01); *B01J 31/0267* (2013.01); *B01J 31/04* (2013.01); *B01J 31/143* (2013.01); *B01J 31/187* (2013.01); *B01J 31/188* (2013.01); *B01J 35/0006* (2013.01); *B01J 37/04* (2013.01); *C07C 2/24* (2013.01); *C07C 2/32* (2013.01); *C07F 9/505* (2013.01); *C07F 9/5022* (2013.01); *C08F 2/40* (2013.01); *C08F 4/69* (2013.01); *C08F 10/00* (2013.01); *C08F 10/02* (2013.01); *C08F 210/16* (2013.01); *C08K 5/00* (2013.01); *C08K 5/05* (2013.01); *C08K 5/17* (2013.01); *B01J 2231/12* (2013.01); *B01J 2231/20* (2013.01); *B01J 2523/67* (2013.01); *B01J 2531/004* (2013.01); *B01J 2531/31* (2013.01); *B01J 2531/62* (2013.01); *C07C 2523/26* (2013.01); *C07C 2531/04* (2013.01); *C07C 2531/14* (2013.01); *C07C 2531/18* (2013.01); *C07C 2531/22* (2013.01); *C07C 2531/24* (2013.01)

(58) Field of Classification Search
CPC ................ C07C 2/32; C07C 2/08; C07C 2/24
USPC .................................................. 585/513, 502
See application file for complete search history.

(56) References Cited

U.S. PATENT DOCUMENTS

| | | | |
|---|---|---|---|
| 2005/0119516 A1 | 6/2005 | Dixon et al. | |
| 2007/0037937 A1* | 2/2007 | Damme | ................ C08F 210/16 526/64 |
| 2007/0232481 A1 | 10/2007 | Zhang et al. | |
| 2011/0124827 A1* | 5/2011 | Godsmark | ................ C07C 2/12 526/64 |
| 2011/0257350 A1 | 10/2011 | Jaber et al. | |
| 2012/0092415 A1 | 4/2012 | Hagiwara et al. | |
| 2012/0142989 A1 | 6/2012 | Jaber et al. | |

(Continued)

FOREIGN PATENT DOCUMENTS

| | | |
|---|---|---|
| CN | 1606538 A | 4/2005 |
| CN | 103270006 A | 8/2013 |

(Continued)

OTHER PUBLICATIONS

Jiang, T. et. al. "The effect of N-aryl bisphosphine ligands on the selective ethylene tetramerization", J. Mol. Catal. A (2008), 279, pp. 90-93. (Year: 2008).*

(Continued)

*Primary Examiner* — Philip Y Louie

(74) *Attorney, Agent, or Firm* — Dentons US LLP

(57) ABSTRACT

A method for olefin oligomerization comprising i) injecting an olefin monomer and a solvent into a continuous stirred tank reactor; ii) injecting an oligomerization catalyst system comprising a ligand compound, a transition metal compound, and a co-catalyst into the continuous stirred tank reactor; and iii) performing a multimerization reaction of the olefin monomer, wherein a ratio of the flowing rates of the olefin monomer and the solvent is from 1:1 to 2:1.

8 Claims, No Drawings

(56) References Cited

U.S. PATENT DOCUMENTS

| | | | |
|---|---|---|---|
| 2012/0172645 A1* | 7/2012 | Sydora | B01J 31/143 585/511 |
| 2013/0090508 A1 | 4/2013 | Wang et al. | |
| 2013/0150642 A1* | 6/2013 | Sydora | B01J 31/04 585/511 |
| 2013/0172651 A1* | 7/2013 | Small | C07C 2/32 585/523 |
| 2014/0011974 A1* | 1/2014 | Noh | C08F 210/16 526/348.2 |
| 2014/0178614 A1* | 6/2014 | Demirors | C08F 210/16 428/35.2 |
| 2015/0031914 A1 | 1/2015 | Gao et al. | |
| 2015/0080629 A1 | 3/2015 | Overett et al. | |
| 2015/0284303 A1 | 10/2015 | Zoricak et al. | |
| 2015/0298110 A1 | 10/2015 | Cho et al. | |
| 2016/0083312 A1 | 3/2016 | Mogorosi et al. | |
| 2017/0267603 A1 | 9/2017 | Im et al. | |
| 2017/0305811 A1 | 10/2017 | Shin et al. | |
| 2018/0009727 A1 | 1/2018 | Hong et al. | |
| 2018/0339289 A1 | 11/2018 | Im et al. | |

FOREIGN PATENT DOCUMENTS

| | | |
|---|---|---|
| CN | 104230908 A | 12/2014 |
| EP | 2987783 A1 | 2/2016 |
| EP | 3257875 A1 | 12/2017 |
| KR | 10-2013-0142151 A | 12/2013 |
| KR | 10-2014-0063346 A | 5/2014 |
| WO | 2013/067620 A1 | 5/2013 |
| WO | 2013/168102 A1 | 11/2013 |
| WO | 2014/094114 A1 | 6/2014 |
| WO | 2014/181248 A1 | 11/2014 |

OTHER PUBLICATIONS

Killian, E. et. al. "The use of bis(diphenylphosphino)amines with N-aryl functionalities in selective ethylene tri- and tetramerization", J. Mol. Catal. A (2007), 270, pp. 214-218 (Year: 2007).*

Anthea Carter et al., "High activity ethylene trimerisation catalysts based on diphosphine ligands", Chemical Communications, 2002, pp. 858-859.

* cited by examiner

METHOD FOR OLEFIN OLIGOMERIZATION

TECHNICAL FIELD

Cross-Reference to Related Applications

This application is a National Stage Application of International Application No. PCT/KR2016/001325 filed on Feb. 5, 2016, which claims the benefit of Korean Patent Application No. 10-2015-0021784 filed on Feb. 12, 2015 and Korean Patent Application No. 10-2015-0176277 filed on Dec. 10, 2015, all of which are hereby incorporated by reference in their entirety for all purposes as if fully set forth herein.

TECHNICAL FIELD

The present invention relates to a method for olefin oligomerization capable of maintaining high linear alpha-olefin selectivity and C2 conversion ratio even with a small amount of a solvent used.

BACKGROUND ART

Linear alpha-olefins are an important material used in a comonomer, a cleaner, a lubricant, a plasticizer, etc. and is widely and commercially used. Particularly, 1-hexene and 1-octene are widely used as the comonomer for controlling the density of a polyethylene during preparing a linear low-density polyethylene (LLDPE).

In a preparation process of a common LLDPE, copolymerization of alpha-olefins, for example, 1-hexene, 1-octene, etc. with ethylene is performed to control density by forming branches at a polymer backbone.

Accordingly, in the preparation of an LLDPE having high comonomer content, the comonomer is a costly part. In order to resolve the drawback, various methods have been conducted.

In addition, the application field or the market size of alpha-olefins is dependent on the kind thereof, and technique on the selective production of a specific olefin is commercially very important. Recently, researches on a technique using a chromium catalyst for preparing 1-hexene or 1-octene with high selectivity via selective ethylene oligomerization are being actively conducted.

The conventional methods of commercially preparing 1-hexene or 1-octene include a shell higher olefin process (SHOP) of Shell Chemicals, a Ziegler process of Chevron Philips chemical, etc. Through the methods, alpha-olefins having wide distribution of $C_4$-$C_{20}$ may be obtained.

As a catalyst for trimerizing ethylene, a chromium-based catalyst using a ligand having the formula of (R1)(R2)X—Y—X(R3)(R4) is suggested. In the formula, X is phosphorus, arsenic or antimony, Y is a linking group such as —N(R5)-, and at least one of R1, R2, R3 and R4 have a polar or electron donating substituent.

In addition, a compound of (o-ethylphenyl)$_2$PN(Me)P(o-ethylphenyl)$_2$ including no polar substituent for at least one of R1, R2, R3 and R4 has been studied as a ligand not exhibiting catalyst activity with respect to 1-hexene under catalytic conditions (*Chem. Commun.*, 2002, 858).

However, the conventional ligand including a heteroatom is still required to have consistently continuous activity on a multimerization reaction and high selectivity during preparing 1-octene or 1-hexene.

Meanwhile, in the conventional ethylene oligomerization, solvents are excessively used, high catalyst activity is exhibited, and high selectivity may be accomplished, however equipments are expanded, and costs and efforts for separating products from solvents are consumed. Therefore, developments on a technique for resolving limitations accompanied with the excessive amount of solvents used are required.

DISCLOSURE OF THE INVENTION

Technical Problem

In the present disclosure, there is provided a method for olefin oligomerization, in which high alpha-olefin selectivity may be attained even with a small amount of a solvent used by controlling the reaction conditions during performing a multimerization reaction using a continuous reaction using a continuous stirred tank reactor.

Technical Solution

According to an aspect of the present invention, there is provided a method for olefin oligomerization comprising:

i) injecting an olefin monomer and a solvent into a continuous stirred tank reactor (CSTR);

ii) injecting an oligomerization catalyst system comprising a ligand compound, a transition metal compound, and a co-catalyst into the continuous stirred tank reactor; and iii) performing a multimerization reaction of the olefin monomer, wherein a ratio of flowing rates of the olefin monomer and the solvent is from 1:1 to 2:1.

Advantageous Effects

According to the method for olefin oligomerization of the present invention, high alpha-olefin selectivity may be attained even with a small amount of a solvent used by controlling the reaction conditions during a multimerization reaction using a continuous reaction using a continuous stirred tank reactor.

BEST MODE FOR CARRYING OUT THE INVENTION

Mode for Carrying Out the Invention

Hereinafter, the present invention will be described in detail to assist the understanding of the present invention. The terms or words used in the present disclosure or claims should not be defined or interpreted in common or dictionary meaning, but should be interpreted as having a meaning that is consistent with their meaning in technical spirit of the present invention on the basis that the inventors may appropriately define the concept of the terms to explain the invention by their best way.

The terminology used herein is for the purpose of describing particular embodiments only and is not intended to limit the present invention. The singular forms are intended to include the plural forms as well, unless the context clearly indicates otherwise.

It will be further understood that the terms "comprises", "comprising", etc. when used in this specification, specify the presence of stated features, numerals, steps, elements or the combination thereof, but do not preclude the presence or addition of one or more other features, numerals, steps, elements or the combination thereof.

In the present disclosure throughout, the terms "catalyst-based", "catalyst composition" or "catalyst system" mean a state obtainable as a catalyst composition having activity by adding three components including a transition metal source, a ligand compound and a co-catalyst, or alternatively, two components including a transition metal compound and a co-catalyst simultaneously or in an optional order. The three components or the two components of the catalyst system may be added in the presence or non-presence of a solvent and a monomer, and the three terms may interchangeably be used.

The term "oligomerization" used in the present disclosure means the oligomerization of olefin. According to the number of the olefin, trimerization, or tetramerization may be referred to, and the general term thereof is multimerization. Particularly, in the present disclosure, the oligomerization means the selective preparation of 1-hexene and 1-octene which are main comonomers of LLDPE from an olefin monomer.

In the present disclosure, a hydrocarbyl group means all compounds composed of only carbon and hydrogen, for example, alkyl, aryl, alkenyl, cycloalkyl, etc., and the hydrocarbyl group may mean both a linear chain and a branched chain unless otherwise referred to and may mean both unsubstituted and substituted type. For example, the alkyl having 1 to 20 carbon atoms may mean methyl, ethyl, propyl, isopropyl, butyl, isobutyl, pentyl, isopentyl, neopentyl, etc., and the aryl having 6 to 20 carbon atoms may mean, for example, phenyl, naphthyl, anthracenyl, etc., without limitation.

In the present disclosure, an alkylaryl group means aryl having at least one alkyl group as a substituent, and an arylalkyl group means alkyl having at least one aryl group as a substituent.

In the present disclosure, a heteroatom means N, O, S or P, and the heterohydrocarbyl may mean hydrocarbyl including at least one heteroatom. That is, the heteroalkyl may mean an alkyl of which one carbon is substituted with a heteroatom or may mean an alkyl including a heteroatom as a substituent. Heteroaryl group may mean an aromatic ring of which one carbon is substituted with a heteroatom such as pyridyl. In addition, the same may go for heteroarylakyl, heteroalkylaryl, heteroalkenylaryl, etc.

In the heterohydrocarbyl group, a linking point for functionalization is carbon, however, in "heteryl group" such as "hydrocarboheteryl group", "organoheteryl group", "heteryl group thereof", etc., the linking point for functionalization may be a heteroatom.

Method for Olefin Oligomerization

The method for olefin oligomerization of the present invention comprises i) injecting an olefin monomer and a solvent into a continuous stirred tank reactor (CSTR); ii) injecting an oligomerization catalyst system comprising a ligand compound, a transition metal compound, and a co-catalyst into the continuous stirred tank reactor; and iii) performing a multimerization reaction of the olefin monomer, wherein the ratio of flowing rates of the olefin monomer and the solvent is from 1:1 to 2:1.

The method for olefin oligomerization of the present invention is a continuous solution polymerization method using a continuous stirred tank reactor (CSTR), and in step i), the olefin monomer and the solvent are injected to the continuous stirred tank reactor (CSTR) so that the olefin monomer is dissolved in the solvent.

Then, in step ii), an oligomerization catalyst system comprising the ligand compound, the transition metal compound and the co-catalyst is injected to the continuous stirred tank reactor, and reactants comprising the olefin monomer, the solvent and the oligomerization catalyst system is injected to the continuous stirred tank reactor. In step iii), the multimerization reaction of olefin is conducted.

As the continuous stirred tank reactor, a commonly used one in the technical field of the present invention may be used, and the configuration thereof is not specifically limited.

In order to maintain high linear alpha-olefin selectivity and C2 conversion ratio even with a small amount of the solvent using a continuous solution polymerization method using the continuous stirred tank reactor, constant reaction conditions, i.e., the temperature, the pressure, and the supplying amounts of the olefin monomer and the solvent are required to be satisfied.

In the method for olefin oligomerization of the present invention, the ratio of the flowing rates of the olefin monomer and the solvent injected to the continuous stirred tank reactor may be from 1:1 to 2:1, and particularly, 1.1:1 to 1.8:1.

In the case where the ratio of the flowing rates of the olefin monomer and the solvent injected to the continuous stirred tank reactor satisfies a range from 1:1 to 2:1, high conversion ratio of the olefin monomer may be accomplished, and the ratio of the solvent relative to the oligomerized product may be lowered.

The multimerization reaction of the olefin in the continuous stirred tank reactor may be performed under a pressure of 30 bar to 150 bar, particularly, 40 bar to 100 bar, and more particularly, 40 bar to 80 bar.

In addition, the multimerization reaction of the olefin in the continuous stirred tank reactor may be performed at the temperature conditions of 30° C. to 150° C., particularly, 40° C. to 120° C., and more particularly, 50° C. to 70° C. In the case where the temperature is 30° C. or more, the reaction may proceed sufficiently in the reactor, and in the case where the temperature is 120° C. or less, the deterioration of process efficiency due to the elevation of the temperature more than needs may be prevented.

The amount of the oligomerization catalyst system c the ligand compound, the transition metal compound and the co-catalyst injected to the continuous stirred tank reactor may be determined to a certain ratio relative to the injection amount of the olefin monomer.

The concentration of the ligand compound in the oligomerization catalyst system injected in step ii) may be from 3 µM to 15 µM, particularly 4 µM to 12 µM, and more particularly, 5 µM to 7 µM.

The concentration of the transition metal compound in the oligomerization catalyst system injected in step ii) may be from 3 µM to 15 µM, particularly 4 µM to 12 µM, and more particularly, 5 µM to 7 µM.

The co-catalyst in the oligomerization catalyst system injected in step ii) may be from 300 to 3,000 equivalents relative to the equivalent of a transition metal included in the transition metal compound, particularly, 400 to 2,000 equivalents, and more particularly, 600 to 1,800 equivalents.

In an embodiment of the present invention, the oligomerized product via step iii) and the solvent satisfy the relation of product/solvent (w/w)>1.0. In the oligomerization of the olefin according to the continuous solution polymerization method using the continuous stirred tank reactor, in order to increase the ratio of the product relative to the solvent, the reaction is required to be performed under constant reaction conditions, and the temperature, the pressure, and the supplying amounts of the olefin monomer and the solvent are required to be satisfied. Therefore, in the case where the conditions of the temperature, the pressure and the supplying amounts of the olefin monomer and the solvent are satisfied, the oligomerized product via step iii) and the solvent may satisfy the relation of product/solvent (w/w) >1.0.

In the case where the olefin monomers are multimerized according to the method for olefin oligomerization of the present invention, the conversion ratio of the product of the olefin monomer may be 60% or more, particularly, 60% to 90%, and more particularly, 65% to 80%.

The olefin monomer may be at least one selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1 eicosene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methylstyrene, divinylbenzene and 3-chloromethylstyrene, and may particularly include ethylene.

Oligomerization Catalyst System
Ligand Compound

The ligand compound included in the oligomerization catalyst system may comprise a diphosphine moiety represented by the following Formula 1.

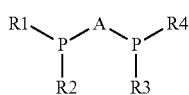

[Formula 1]

In the above Formula 1, A is N, As or Sb, and R1 to R4 are each independently hydrocarbyl, heterohydrocarbyl or hydrocarbylheteryl having 1 to 20 carbon atoms.

In addition, the ligand compound comprising the diphosphine moiety represented by Formula 1 may comprise at least two diphosphine moieties represented by the following Formula 2.

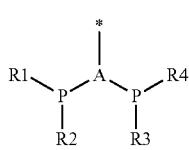

[Formula 2]

In the above Formula 2, A and R1 to R4 are the same as defined in Formula 1, and * is a linker connecting at least two diphosphine moieties.

Further, in the case that the number of the diphosphine moiety represented by the above Formula 2 is two, and A is nitrogen (N), the ligand compound may comprise a compound represented by the following Formula 2a.

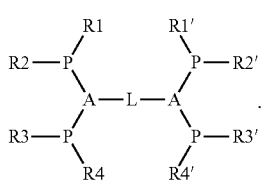

[Formula 2a]

In the above Formula 2a, each of R1 to R4 and R1' to R4' may be selected from the same group as R1 to R4 in Formula 1 or 2, and L may be a linker connecting two diphosphine moieties.

Examples of R1 to R4 in Formulae 1, 2 and 2a and R1' to R4' in Formula 2a are not specifically limited, however may be, for example, aryl, heteroaryl or arylheteryl having 6 to 20 carbon atoms; or alkylaryl, heteroalkylaryl, alkylheteroaryl or alkylarylheteryl having 7 to 20 carbon atoms. In the case that such substituents are selected, positive influences on the activity of the catalyst or the selectivity of linear alpha-olefins may be obtained.

The linker (L) connecting at least two diphosphine moieties may be a hydrocarbyl group having various structures, and the carbon number between the diphosphine moieties with the shortest distance may be from 2 to 30. That is, the hydrocarbyl group is provided for the connection between two or more diphosphine moieties, and the carbon number in the hydrocarbyl group for connecting the diphosphine moieties with the shortest distance may be in a range of 2 to 10.

Particularly, the linker may be combined with at least one selected from the group consisting of an aliphatic group having 2 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a hetero aromatic group having 6 to 20 carbon atoms, and may have any structure, without specific limitation only if satisfying the above conditions.

In addition, in the case that at least one selected from the above group or a group obtained by combining at least two thereof is determined as a main chain, the main chain of the linker may have a substituent with diverse structures.

Particularly, the substituent of the linker may be at least one selected from the group consisting of an aliphatic group having 1 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a hetero aromatic group having 6 to 20 carbon atoms. One, two or more of the substituents may be combined with the main chain, and the combining position may preferably be a far side from the diphosphine moiety in consideration of the flexibility of the linker, however the combining position of the substituent is not specifically limited thereto.

Non-limiting examples of the linker (L) for connecting at least two groups represented by the above Formula 1 via 2 to 30 carbon atoms may comprise a compound having an aliphatic group having 2 to 30 carbon atoms (for example, an alkylene group, an alkenylene group, an alkynylene group, or a hetero aliphatic group including a heteroatom in the aliphatic group), an alicyclic group having 2 to 20 carbon atoms (for example, a cycloalkylene group, a cycloalkenylene group, a cycloalkenylene group, or a hetero alicyclic group including a heteroatom in the alicyclic group), or a combined group of the aliphatic (or hetero aliphatic) group and the alicyclic (or hetero alicyclic) group.

According to another embodiment of the present invention, the ligand compound may comprise a compound represented by the following Formula 3.

[Formula 3]

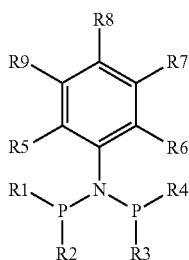

In Formula 3, R1 to R4 are each independently aryl having 6 to 20 carbon atoms or alkylaryl having 7 to 20 carbon atoms, and R5 is alkyl having 1 to 20 carbon atoms.

In the case that R5 is methyl, R6 may be a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In addition, in the case that R5 is methyl, R6 may preferably be heteroalkyl, heteroalkenyl, heteroarylalkyl, heteroarylalkenyl, or a heteryl group thereof having 2 to 20 carbon atoms; heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 may be alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 may be each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

As described above, the ligand compound represented by Formula 3 may be, for example, a compound obtained by substituting carbon atoms at positions 2 and 6 in an aniline compound with R5 and R6, and the properties of the ligand compound and the oligomerization catalyst system including the same may be changed according to the substituent for the carbon atoms at positions 2 and 6.

In the case where a methyl group is substituted for the carbon atom at position 2, a group different from the substituent at position 2 may be substituted for the carbon atom at position 6 to attain an asymmetric structure.

As non-limiting examples, a linear group of an alkyl group, an alkenyl group, a heteroalkyl group, a heteroalkenyl group, or the heteryl group thereof having 2 or 3 carbon atoms may be substituted; or an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 4 to 20 carbon atoms may be substituted.

In addition, a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteroaryl group thereof having 6 to 20 carbon atoms may be substituted; or an alkylaryl group, a heteroalkylaryl group, or the heteryl group thereof having 7 to 20 carbon atoms may be substituted.

In addition, in the case where an alkyl group having 2 to 20 carbon atoms is substituted for the carbon atom at position 2, a substituent same as or different from the substituent at position 2 may be substituted for the carbon atom at position 6.

As non-limiting examples, an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 2 to 20 carbon atoms may be substituted; a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

Due to the structural characteristics of the substituent groups of the aniline group, in the catalyst system including the ligand compound, PNP—Cr may easily interact according to various conditions such as electronic and steric circumstances around a transition metal, and the high activity of an oligomerization reaction may be attained. Particularly, high selectivity may be attained particularly for 1-hexene, 1-octene, etc., and incidentally, energy may be saved, because a separating process may become unnecessary according to the increase of 1-hexene and the decrease of the isomer of 1-hexene.

The ligand compound may be synthesized by the following Reaction 1, without limitation.

[Reaction 1]

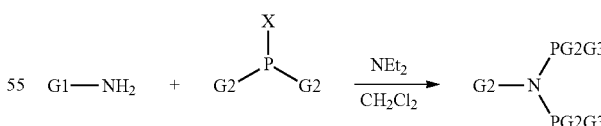

In the above Reaction 1, G1 may be a phenyl group having R5 to R9 in Formula 3, each of G2 and G3 may be R1 to R4 in Formula 3, and X may be halogen.

Reaction 1 is a general reaction for synthesizing a ligand compound represented by Formula 3 and may be a reaction for producing diphosphinoamine via the reaction of an amine and phosphine. That is, in the reaction, the amine as a nucleophile may push a leaving group represented by X in the phosphine for substitution. X may be any functional group which may be easily separated and stabilized, without limitation. Typically, halogens such as Cl, Br or I may be included.

Transition Metal Compound

Such a selective olefin oligomerization reaction is closely concerned with a catalyst system used. The catalyst system used for the oligomerization reaction of olefin includes a transition metal compound which plays the role of a main catalyst and a co-catalyst. In this case, according to the chemical structure of the ligand, the structure of an active catalyst may be changed, and so, olefin selectivity, activity or the amount of by-products may be changed.

The transition metal compound in the oligomerization catalyst system according to an embodiment of the present invention acts as a main catalyst and may have a state making a coordination bond with the ligand compound as described above.

Particularly, the transition metal compound and the ligand compound including at least two diphosphine moieties represented by the above Formula 2 may make a coordination bond as represented in the following Formula 2-1.

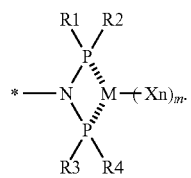

[Formula 2-1]

In the above Formula 2-1, R1 to R4 are the same as defined in Formula 1 and * is the same as defined in Formula 2, M may be a transition metal, and preferably, Cr, Xn may be H, F, Cl, Br, I, alkyl, alkenyl, arylalkyl, heteroalkyl, heteroalkenyl or heteroarylalkyl having 1 to 6 carbon atoms, halogen, acetate, or acetyl acetonate, and m is an oxidation number of M and may be a natural number.

In addition, the transition metal compound and the ligand compound represented by Formula 2a may make a coordination bond as shown in the following Formula 2a-1.

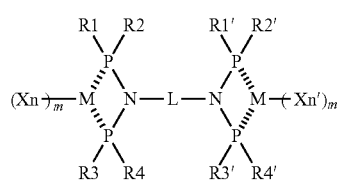

[Formula 2a-1]

In Formula 2a-1, R1 to R4, Xn, m and M are the same as defined in Formula 2-1, and R1' to R4' and Xn' are also the same as R1 to R4.

In addition, the transition metal compound and the ligand compound represented by Formula 3 may make a coordination bond as shown in the following Formula 3-1.

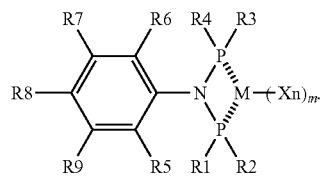

[Formula 3-1]

In Formula 3-1, Xn, m and M are the same as defined in Formula 2-1, and R1 to R9 are the same as defined in Formula 3.

Particularly, the transition metal compound may include an organochromium compound, and the organochromium compound may be at least one selected from the group consisting of chromium(III)acetylacetonate, trichlorochromiumtristetrahydrofuran, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate and chromium(III)acetatehydroxide.

Co-Catalyst

The co-catalyst is an organometallic compound including a metal in group 13 and may be generally any one which may be used for multimerizing olefin in the presence of a transition metal compound catalyst, without specific limitation. Particularly, the co-catalyst may be at least one selected from the group consisting of the compounds represented by the following Formulae 4 to 6.

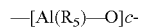—[Al(R$_5$)—O]c-     [Formula 4]

In the above Formula 4, each R$_5$ is the same or different from each other and is independently a halogen radical, a hydrocarbyl radical having 1 to 20 carbon atoms, or a halogen substituted hydrocarbyl radical having 1 to 20 carbon atoms, and c is an integer of at least 2.

D(R$_6$)$_3$     [Formula 5]

In the above Formula 5,

D is aluminum or boron, each R$_6$ is the same or different from each other and is independently hydrogen or halogen, a hydrocarbyl having 1 to 20 carbon atoms, or halogen substituted hydrocarbyl having 1 to 20 carbon atoms.

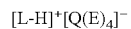[L-H]$^+$[Q(E)$_4$]$^-$     [Formula 6]

In the above Formula 6,

L is a neutral Lewis base, [L-H]$^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

The compound represented by Formula 4 may be modified methyl aluminoxane (MAO), methyl aluminoxane (MAO), ethyl aluminoxane, isobutyl aluminoxane, butyl aluminoxane, etc.

The alkyl metal compound represented by the above Formula 5 may comprise, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc.

Examples of the compound represented by the above Formula 6 may comprise, for example, triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, etc.

The co-catalyst of the oligomerization catalyst system according to an embodiment may preferably comprise aluminoxane, and more preferably, methyl aluminoxane (MAO) or modified methyl aluminoxane (MMAO) may be used.

Method for Preparing the Oligomerization Catalyst System

Non-limiting examples of the method for preparing the oligomerization catalyst system may comprise a step of preparing a catalyst composition by mixing the ligand compound and a transition metal compound; and a step of mixing a co-catalyst and the catalyst composition at a temperature of −40 to 80° C. and activating.

The catalyst composition comprises the ligand compound and the transition metal compound, and according to the method for preparing the oligomerization catalyst system according to the present invention, the ligand compound and the transition metal compound are mixed in advance to induce a metalation reaction between the two compounds.

The metalation reaction may be a reaction for making a coordination bond between the ligand compound and the transition metal compound, and the coordination state of the ligand compound and the transition metal compound, the activation point of the ligand compound, etc. will be explained below.

After a catalyst composition is prepared via a sufficient metalation reaction of the ligand compound and the transition metal compound, the catalyst composition and a co-catalyst are mixed and activated. The activation may mean activation by an oligomerization catalyst system via the contact and aging of the catalyst composition and the co-catalyst.

The activation of the catalyst composition and the co-catalyst may be performed by contacting the co-catalyst and the catalyst composition present as a solution phase after being mixed with an organic solvent, and aging for a certain time period. The activation may be performed by stirring, simple mixing, etc., without specific limitation, and any method for generating the activity as the oligomerization catalyst system via the contact of the catalyst composition and the co-catalyst may be applied.

The organic solvent may include, for example, heptane, toluene, cyclohexane, methylcyclohexane, 1-hexene, diethyl ether, tetrahydrofuran, acetonitrile, dichloromethane, chloroform, chlorobenzene, methanol, acetone, etc., without limitation.

The activation of the catalyst composition and the co-catalyst may be performed at a temperature from −40 to 80° C., and preferably, from 20 to 80° C. or from 25 to 60° C. In the case that the contact and aging of the catalyst composition with the co-catalyst for activation is performed at a high temperature greater than 80° C., the ligand and the transition metal of the catalyst composition may be excessively activated by an alkyl metal possibly used as the co-catalyst, and by-products may be produced during an oligomerization reaction or the activity may be deteriorated at an early stage.

In addition, in the case that the contact and aging of the catalyst composition with the co-catalyst for activation is performed at an extremely low temperature less than −40° C., energy necessary for the activation of a catalyst may not be supplied, and the catalyst may not be activated.

The activation of the catalyst composition and the co-catalyst may be attained by the contact of the co-catalyst and the catalyst composition present as a solution phase after being mixed with an organic solvent, and aging for a certain time period. The activation may be performed by stirring, simple mixing, etc., without specific limitation, and any method for generating the activity via the contact of the catalyst composition and the co-catalyst as the oligomerization catalyst system may be applied.

The co-catalyst and the catalyst composition may be fed via separate and independent lines, and the reactant may be directly fed to the reactor via a separate line. Accordingly, the contact time with the reactant may decrease, and the maintenance of the activity at a high temperature may be attained.

EXAMPLES

Hereinafter, examples of the present invention will be explained in detail so that a person skilled in the art may easily perform. However, the present invention may be embodied in various modifications and is not limited to the examples herein.

<Synthesis of Ligand Compound>

All reactions were performed under an argon atmosphere using Schlenk technique or a glove box. The ligands synthesized were analyzed after taking $^1$H (500 MHz) and $^{31}$P (202 MHz) NMR spectra using a Varian 500 MHz spectrometer. Chemical shift values were represented by ppm downfield from TMS with a residual solvent peak as a reference. A phosphorous probe was calibrated using aqueous $H_3PO_4$.

Preparation Example

Under an argon atmosphere, 3-(aminomethyl)-3,5,5-trimethylcyclohexaneamine (5 mmol) and triethylamine (3-10 eq. to amine) were dissolved in dichloromethane (80 ml). To a flask in a water bath, chloroditolylphosphine (20 mmol, 2 eq. to amine) was slowly added and stirred overnight. After evaporating solvents by applying vacuum, THF was added and sufficiently stirred. A triethylammonium chloride salt was removed using an air-free glass filter. Solvents were removed from the filtrate to obtain a product.

<Preparation of Alpha-Olefin Oligomer>

Example 1

Under an argon gas atmosphere, the ligand compound prepared according to the preparation example and Cr(acac)3 (17.5 mg, 0.014 mmol) were added to a flask so that the molar ratio of ligand:chromium was 0.55:1, and 100 ml of methylcyclohexane (MCH) was added thereto, followed by stirring to obtain a 0.5 mM (to Cr) solution.

To a 2 L, CSTR under a nitrogen atmosphere, methylcyclohexane and ethylene were continuously injected with the flowing rates of 1.0 kg/hr and 1.5 kg/hr, respectively to maintain the pressure to 60 bar. The solution with 0.5 mM (to Cr) prepared above was injected to a 10 L, pressure vessel, and then, a catalyst solution appropriately diluted in cyclohexane was injected to the reactor in a rate of 3 mL/min, and a solution obtained by diluting a modified methylaluminoxane (MMAO) co-catalyst in cyclohexane was continuously injected (5.4 mL/min) in consideration of the injection amount of the catalyst solution so that the molar ratio of Al:Cr was 1,800:1. The reaction temperature was controlled to 60° C. by continuously injecting water of room temperature to the jacket of the reactor. Under the circumstance of performing the reaction for 2 hours stably, 50 mL of the reactant discharged was collected for 1 hour and quenched with water. An organic layer was filtered using a PTFE syringe filter, and GC analysis was conducted.

400 ml of ethanol/HCl (10 vol %) was added to the remaining reaction product, followed by stirring and filtering to obtain a polymer. The polymer thus obtained was dried at 60 in a vacuum oven overnight, and the weight was measured.

Examples 2 to 6 and Comparative Example 1

Alpha-olefin oligomers were prepared according to the same method described in step 2 in Example 1 except for setting the flowing rates of methylcyclohexane and ethylene, and the injection rates of a catalyst solution and a co-catalyst as shown in the following Table 1.

TABLE 1

|  | injection | | | | activity |
|---|---|---|---|---|---|
|  | ethylene | MCH | catalyst | MMAO |  |
|  | Kg/h | | mL/min | | ton/mol Cr |
| Example 1 | 1.5 | 1 | 3 | 5.4 | 119.9 |
| Example 2 | 1.75 | 1.17 | 3.5 | 6.3 | 127.8 |
| Example 3 | 1.75 | 1 | 4 | 7.2 | 101.0 |
| Example 4 | 1.75 | 1 | 3 | 5.4 | 134.5 |
| Example 5 | 1.75 | 1 | 2 | 3.6 | 171.7 |
| Example 6 | 1.75 | 1 | 2.5 | 4.5 | 153.4 |
| Comparative Example 1 | 1 | 1.2 | 5.5 | 10.6 | 46.8 |

Experimental Example 1: Activity of Catalyst

Referring to Table 1, the examples according to exemplary embodiments of the method for olefin oligomerization of the present invention were secured to have very high activity in a multimerization reaction.

Experimental Example 2: Oligomerization Reaction According to Injection Rates of Olefin Monomer, Solvent and Oligomerizing Catalyst System The results of Examples 1 to 6 are shown in the following Table 2.

TABLE 2

|  | $1\text{-}C_6$ wt % | $1\text{-}C_8$ wt % | $C_{10}\text{-}C_{40}$ wt % | $1\text{-}C_6 +$ $1\text{-}C_8$ wt % | $1\text{-}C_6 +$ $1\text{-}C_8 +$ $C_{10}\text{-}C_{40}$ wt % | $C_6$ isomer wt % | product/ solvent (w/w) |
|---|---|---|---|---|---|---|---|
| Example 1 | 40 | 45.9 | 11.8 | 85.9 | 97.7 | 1.6 | 1.08 |
| Example 2 | 39.1 | 47.2 | 11.6 | 86.3 | 97.8 | 1.5 | 1.15 |
| Example 3 | 40.2 | 45.6 | 12.7 | 85.9 | 98.5 | 1.6 | 1.21 |
| Example 4 | 37.1 | 49 | 11.7 | 86.1 | 97.8 | 1.6 | 1.21 |
| Example 5 | 30 | 57.9 | 9.8 | 87.9 | 97.7 | 1.6 | 1.03 |
| Example 6 | 32.4 | 54.6 | 10.6 | 87.1 | 97.6 | 1.7 | 1.15 |
| Comparative Example 1 | 38.7 | 41.4 | 17.2 | 80.2 | 97.4 | 1.8 | 0.64 |

Referring to Tables 1 and 2, in the method for olefin oligomerization according to Examples 1 to 6 of the present invention, during performing a multimerization reaction of the olefin monomer after injecting an olefin monomer and a solvent together to a continuous stirred tank reactor (CSTR), and then injecting an oligomer catalyst system, since the ratio of the flowing rates of the olefin monomer and the solvent satisfies a range of 1:1 to 2:1, the oligomerized product and the solvent may satisfy the relation of product/solvent (w/w)>1.0. Accordingly, oligomerized olefin may be produced with high yield even with a small amount of a solvent used, and high linear alpha-olefin selectivity may be maintained.

On the contrary, in the method for olefin oligomerization according to Comparative Example 1, since the ratio of the flowing rates of the olefin monomer and the solvent (1:1.2) does not satisfy the range of 1:1 to 2:1, product/solvent (w/w)=0.64, and the amount of the solvent is greater when compared to that of the oligomerized product.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:

1. A method for oligomerizing ethylene, the method comprising:
   i) injecting ethylene and a solvent into a continuous stirred tank reactor;
   ii) injecting an oligomerization catalyst system comprising a ligand compound, an organic chromium compound, and a co-catalyst into the continuous stirred tank reactor; and
   iii) oligomerizing the ethylene in the continuous stirred tank reactor to produce an oligomerization product, wherein a ratio of mass flow rates of the ethylene and the solvent is from 1.5:1 to 1.75:1, such that a weight ratio of the oligomerization product to the solvent is >1.0,
   wherein the solvent is selected from the group consisting of heptane, toluene, cyclohexane, methylcyclohexane, 1-hexene, diethyl ether, tetrahydrofuran, acetonitrile, dichloromethane, chloroform, chlorobenzene, methanol, and acetone, wherein the ligand compound comprises at least two diphosphine moieties represented by the following Formula 2:

[Formula 2]

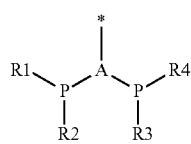

wherein in Formula 2, A is N, As or Sb, and R1 to R4 are each independently alkylaryl having 7 to 20 carbon atoms, wherein * is a hydrocarbyl linker connecting the at least two diphosphine moieties, wherein a carbon number of the shortest distance between the at least two diphosphine moieties is from 2 to 30, and wherein the linker connecting the at least two diphosphine moieties comprises a combination of at least one aliphatic group having 2 to 20 carbon atoms and at least one alicyclic group having 3 to 20 carbon atoms such that the at least one aliphatic group is directly bonded to group A of one of the at least two diphosphine moieties and the at least one alicyclic group is directly bonded to group A of the other of the at least two diphosphine moieties.

2. The method for oligomerizing ethylene of claim 1, wherein the oligomerization of ethylene in the continuous stirred tank reactor is conducted under a pressure of 30 bar to 150 bar.

3. The method for oligomerizing ethylene of claim 1, wherein the oligomerization of ethylene in the continuous stirred tank reactor is conducted at a temperature of 30° C. to 150° C.

4. The method for oligomerizing ethylene of claim 1, wherein a concentration of the ligand compound of the oligomerization catalyst system injected in step ii) is from 3 µM to 15 µM.

5. The method for oligomerizing ethylene of claim 1, wherein an amount of the co-catalyst of the oligomerization catalyst system injected in step ii) is from 300 equivalents to 3,000 equivalents relative to an equivalent of chromium included in the organic chromium compound.

6. The method for oligomerizing ethylene of claim 1, wherein the oligomerization catalyst system is produced by a method comprising:
preparing a catalyst composition by mixing the ligand compound and the organic chromium compound; and
mixing the co-catalyst and the catalyst composition and activating the resulting mixture at a temperature of −40° C. to 80° C.

7. The method for oligomerizing ethylene of claim 1, wherein the organic chromium compound comprises at least one selected from the group consisting of chromium(III) acetyl acetonate, trichlorochromium tris tetrahydrofuran, chromium(III)-2-ethylhexanoate, chromium(III) tris (2,2,6,6-tetramethyl-3,5-heptanedioate), chromium(III) benzoyl acetonate, chromium(III) hexafluoro-2,4-pentanedionate, and chromium(III)acetate hydroxide.

8. The method for oligomerizing ethylene of claim 1, wherein the co-catalyst is at least one selected from compounds represented by the following Formulae 4 to 6:

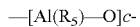 [Formula 4]

wherein in Formula 4, each $R_5$ is the same or different and is independently a halogen, a hydrocarbyl group having 1 to 20 carbon atoms, or a halogen substituted hydrocarbyl group having 1 to 20 carbon atoms, and c is an integer of at least 2;

 [Formula 5]

wherein in Formula 5, D is aluminum or boron, each $R_6$ is the same or different and is independently hydrogen or a halogen, a hydrocarbyl group having 1 to 20 carbon atoms, or a halogen substituted hydrocarbyl group having 1 to 20 carbon atoms;

 [Formula 6]

wherein in Formula 6, L is a neutral Lewis acid, $[L-H]^+$ is a Brønsted acid, Q is boron or aluminum with an oxidation state of +3, and each E is independently an aryl group having 6 to 20 carbon atoms or an alkyl group having 1 to 20 carbon atoms, where at least one hydrogen atom is optionally substituted with a halogen, a hydrocarbyl group having 1 to 20 carbon atoms, an alkoxy functional group or a phenoxy functional group.

* * * * *